United States Patent [19]
Buchert

[11] Patent Number: 5,823,966
[45] Date of Patent: *Oct. 20, 1998

[54] NON-INVASIVE CONTINUOUS BLOOD GLUCOSE MONITORING

[76] Inventor: Janusz Michal Buchert, 180 Cabrini Blvd., #79, New York, N.Y. 10033

[*] Notice: The term of this patent shall not extend beyond the expiration date of Pat. No. 5,666,956.

[21] Appl. No.: 859,579

[22] Filed: May 20, 1997

[51] Int. Cl.$^6$ .................................................. A61B 6/00
[52] U.S. Cl. ............................................................. 600/473
[58] Field of Search ........................... 600/310, 314–316, 600/322–328, 339–342, 473, 475; 356/39–41

[56] References Cited

U.S. PATENT DOCUMENTS

| | | |
|---|---|---|
| 3,958,560 | 5/1976 | March . |
| 4,790,324 | 12/1988 | O'Hara et al. . |
| 4,797,840 | 1/1989 | Fraden . |
| 4,882,492 | 11/1989 | Schlager . |
| 4,890,621 | 1/1990 | Hakky ..................................... 600/316 |
| 5,024,533 | 6/1991 | Egawa et al. . |
| 5,086,229 | 2/1992 | Rosenthal et al. . |
| 5,115,133 | 5/1992 | Knudson . |
| 5,127,742 | 7/1992 | Fraden . |
| 5,146,091 | 9/1992 | Knudson . |
| 5,159,936 | 11/1992 | Yelderman et al. . |
| 5,178,464 | 1/1993 | Fraden . |
| 5,179,951 | 1/1993 | Knudson . |
| 5,313,941 | 5/1994 | Braig et al. . |
| 5,313,951 | 5/1994 | Zhao . |
| 5,368,038 | 11/1994 | Fraden . |
| 5,370,114 | 12/1994 | Wong et al. . |
| 5,383,452 | 1/1995 | Buchert . |
| 5,402,778 | 4/1995 | Chance .................................. 600/310 |
| 5,452,716 | 9/1995 | Clift . |
| 5,460,177 | 10/1995 | Purdy et al. . |
| 5,469,855 | 11/1995 | Pompei et al. . |
| 5,515,847 | 5/1996 | Braig et al. . |
| 5,615,672 | 4/1997 | Braig et al. . |
| 5,626,139 | 5/1997 | Szeles et al. . |
| 5,653,239 | 8/1997 | Pompei et al. . |
| 5,666,956 | 9/1997 | Buchert .................................. 600/316 |

OTHER PUBLICATIONS

Hamamatsu Catalog "Infrared Detectors" Sep. 1993 pp. 26–27.
Meggitt Avionics Inc. "Thermopile Detectors" catalog cards 1996.

*Primary Examiner*—Jennifer Bahr
*Assistant Examiner*—Bryan K. Yarnell

[57] ABSTRACT

A method and an instrument for a continuous non-invasive detection of an analyte (e.g. glucose) concentration in a human body tissue such as blood is discussed herein. The instrument remote sensor assembly mounted in subject's ear canal continuously measures analyte concentration by detecting the infrared radiation naturally emitted by a human body. It uses an infrared detector with a combination of adequate filters such as, for example, a negative correlation filter or narrow band filters or other detector-filter assemblies. The method and instrument is based on the discovery that natural infrared emission from the human body, especially from the tympanic membrane, is modulated by the state of the emitting tissue. Spectral emissivity of human infrared radiation from the tympanic membrane consists of spectral information of the tissue (e.g. blood) analyte (e.g. glucose). This can be directly correlated with the blood analyte concentration, for example, the blood glucose concentration.

9 Claims, 4 Drawing Sheets

FIG. 4c  FIG. 4d
TOP VIEW
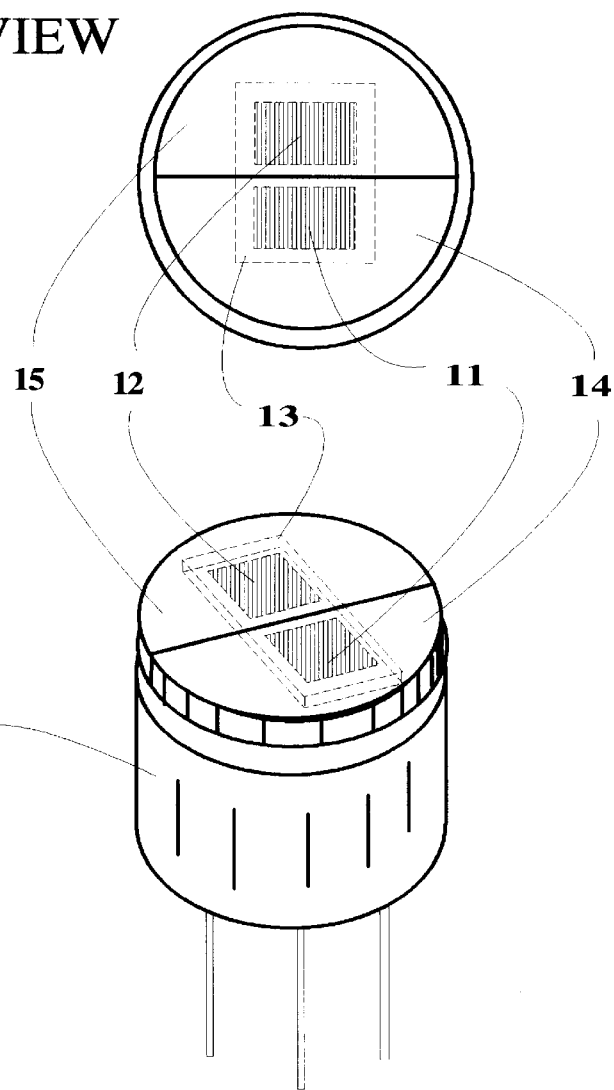
FIG. 4a  FIG. 4b

NON-INVASIVE CONTINUOUS BLOOD GLUCOSE MONITORING

CROSS-REFERENCE TO RELATED APPLICATIONS

This application is related to the U.S. patent application Ser. No. 08/650,832, filed May 20, 1996 now U.S. Pat. No. 5,666,956.

BACKGROUND OF THE INVENTION

1. Field of the Invention

The present invention relates to a spectroscopic method for continuously measuring the concentration changes of glucose in human blood using a non-invasive technique which does not require taking a sample from the body for examination. It includes a method and instrument for detecting continuously the infrared radiation naturally emitted by the human body through the use of an infrared detector with a combination of adequate filters or other detector-filter assemblies to measure the intensity of emission lines characteristic to the body analyte in an infrared spectral region emitted as heat.

2. Related Art

The current state of the art in measuring sugar levels in body liquids or foods, fruits and other agricultural products requires taking a sample from the object during the examination process. Special instruments are available for determining blood glucose levels in people with diabetes. The technology uses a small blood sample obtained from a finger prick. The blood is placed on chemically prepared strips and inserted into a portable instrument which analyzes it and provides a blood glucose level measurement. Diabetics must prick their fingers to draw blood for monitoring their glucose levels and some of them must do this many times a day. Thus, there is a need for continuous non-invasive blood glucose monitoring for use in controlling the regulated insulin reservoir (such as an insulin pump or artificial pancreas) in implants or automatic insulin control systems.

To eliminate the pain of drawing blood, as well as to eliminate a source of potential infection, non-invasive optical methods for measuring sugar in blood were invented. They use absorption, transmission, reflection or luminescence methods for spectroscopically analyzing blood glucose concentrations and are described in many patents listed in the REFERENCE CITED part of this patent.

Other patents for non-invasively analyzing glucose levels in blood are based on various spectroscopic, electrochemical and acoustic velocity measurement methods.

In U.S. Pat. Nos. 5,515,847 and 5,615,672 by Braig et al. is shown a method and apparatus for monitoring glucose, ethyl alcohol and other blood constituents in a noninvasive manner. The measurements are made by monitoring infrared absorption of the desired blood constituent in the long infrared wavelength range where the blood constituent has a strong and distinguishable absorption spectrum. The long wavelength infrared energy emitted by a person as heat is monitored and used as a source of infrared energy for the measurements of the infrared absorption of particular constituents in the blood at characteristic infrared absorption wavelengths for those constituents. The measurements are preferably synchronized with the systole and distole of the cardiac cycle so that the signal contribution caused by veins and tissues (which do not pulse) may be cancelled when a ratio of the detected signals is taken. A temperature sensing device for measuring a person's internal temperature at the arm or other vascularized appendage is also used in adjusting the constituent concentration measurement for temperature dependent effects.

In U.S. Pat. No. 5,666,956 by Buchert is shown an instrument and method for non-invasive monitoring of human body tissue analyte by measuring the body's infrared radiation e.g. emission spectral lines characteristic to tissue analytes. It is based on the discovery that natural infrared emission from the human body, especially from the tympanic membrane (which has the properties of a blackbody cavity), is modulated by the state of the emitting tissue. Spectral emissivity of human infrared radiation from the tympanic membrane consists of spectral information of the blood analyte. This spectral emissivity is measured as heat emitted by the body. It consists of a spectral emission band and lines characteristic to tissue analyte and can be directly correlated with the blood analyte concentration, for example, the glucose concentration.

State of the art non-invasive blood glucose measurement devices contain many approaches and indicate the importance of the problem. None of these devices have yet been marketed. Some inventors claim that the instruments being developed give accurate blood glucose level readings and can be used for home testing by diabetics. These instruments have limitations stemming from the use of near infrared light for measurement of absorption, transmission or reflectance; in this region of the spectrum one can observe interference in absorption from other chemical components. Analyses based on only one or two wavelengths can be inaccurate if there is alcohol in the blood or any other substances that absorb at the same frequencies. In addition, these analyses can be thrown off by instrument errors, outlier samples (samples with spectra that differ from the calibration set) physiological differences between people (skin pigmentation, thickness of the finger). Methods of near infrared spectroscopy must be coupled with sophisticated mathematical and statistical techniques to distinguish between non-glucose sources and to extract a faint glucose spectral signature. Another limitation of these types of blood glucose testers is that they must be custom calibrated for each user. The need for individual calibration results from the different combination of water levels, fat levels and protein levels in people which cause changes in the absorption of near infrared light. Since the amount of glucose in the body is less than one thousandth that of other chemicals (and all of them possess absorption in the near infrared), variations of these constituents, which exist among people, may make universal calibration unlikely.

Other, non-invasive but also non-direct methods and instruments attempt to determine blood glucose content by measuring the glucose in sweat, saliva, urine or tears. These measurements, which can be quite reliable from the chemical analysis point of view, do not determine blood glucose levels because of the complicated, and not always well-defined, relationship between blood glucose levels and glucose concentration in other body fluids. Other invented methods like acoustic velocity measurements in blood, are not very reliable because of the lack of a well established and simple relationship to blood glucose levels.

With the exception of Braig et al. U.S. Pat. Nos. 5,515,847 and 5,615,672 and Buchert U.S. Pat. No. 5,666,956, none of the above described methods and devices for the non-invasive measurement of blood glucose, or other biological constituents of the human body, explore the fact that the human body naturally emits very strong electromagnetic signals in the micrometer wavelength. Non-invasive optical methods already invented for sugar determination use absorption, transmission, reflection, luminescence or scattering methods in near-infrared or infrared spectral regions for spectroscopically analyzing blood glucose concentrations. As in standard spectroscopical methods one needs a source of electromagnetic radiation in certain wavelengths and a means of detecting the resulting transmitted, absorbed, luminescence radiation after it undergoes interaction with a measured medium, e.g. blood or other tissue, to determine the concentration of biological constituents of the human body using a number of technical approaches.

Infrared sensing devices have been commercially available for measuring the temperature of objects. Infrared thermometry is used in industry to measure remotely processes and machinery temperatures. In medical applications these methods are used to measure patient temperatures without physical contact. One can measure a patient's skin temperature or, more reliably, a patient's temperature by quantifying the infrared emission from the tympanic membrane. The tympanic membrane is known to be in an excellent position for the measurement of body temperature because it shares its blood supply with the hypothalamus, the center of the core of body temperature regulation. The tympanic thermometer uses the ear. It is inserted into the auditory canal so as to sufficiently enclose the detector apparatus such that multiple reflections of radiation from the tympanic membrane transform the auditory canal into a "black body" cavity, a cavity with emissivity theoretically equal to one. In this a way the sensor can get a clear view of the tympanic membrane and its blood vessels to determine the amount of infrared radiation emitted by the patient's tympanic membrane.

Plank's law states a relationship between radiant intensity, spectral distribution and temperature of the blackbody. As temperature rises, radiation energy is increased. Radiation energy varies depending on wavelengths. The peak value of the radiant emittance distribution shifts to the short wavelengths side with an increase in temperature, and radiation occurs over a wide wavelength band. Total energy radiated from the blackbody and measured by a noncontact infrared thermometer is the result of the total energy emitted over all wavelengths. It is proportional to an integral of Planck's equation with respect to all wavelengths. It is described in physics by the StefanBoltzman law.

A number of U.S. patents describe a different idea and design of tympanic, noncontact thermometers. One can reference: U.S. Pat. No. 4,790,324 to G. J. O'Hara; U.S. Pat. Nos. 4,932,789 and 5,024,533 to Shunji Egawa et al.; U.S. Pat. Nos. 4,797,840 and 5,178,464 to J. Fraden; U.S. Pat. No. 5,159,936 to M. Yelderman et al.; U.S. Pat. No. 5,167,235 to A. R. Seacord et al.; and U.S. Pat. No. 5,169,235 to H. Tominaga et al. In these patents various technical approaches are described concerning stabilization and calibration of such noncontact thermometers. Commercially few such thermometers are available. These include: Thermoscan Instant Thermometer Model No. HM-2 for home use by Thermoscan Inc., 6295 Ferris Square, Suite G, San Diego, Calif. 92121-3248 and other instruments such as Thermoscan PRO-1 and PRO-LT for clinical use and the "GentleTemp" model MC-502 ear thermometer by OMRON Healthcare Inc., 300 Lakeview Parkway, Vernon Hills, Ill. 60061.

SUMMARY OF THE INVENTION

It is a principal object of the present invention to provide an instrument and method for noninvasive continuous blood glucose concentration measurements, which can analyze emission spectral lines at the natural emission fingerprints region of glucose in the infrared spectral region.

It is the further object of the present invention to provide an instrument for continuous noninvasive blood glucose concentration determination. The said instrument in the form of a remote sensor assembly mounted in a subject's ear canal continuously measures the emission intensity of a spectral emission band of glucose in blood in an infrared spectral region.

It is still the further object of this invention to provide a technique for detecting the presence of glucose molecules in the human body by means of continuous measurements of the emission intensity of the analyte characteristic bands in the infrared spectral region utilizing a non-dispersive correlation spectroscopy method.

It is another object of this invention to provide instruments and methods to measure continuously electromagnetic radiation emitted from the human body which has been spectrally modified by the presence of glucose utilizing a negative correlation filter for the detection of said radiation in the infrared spectral region.

It is still another object of this invention to provide instruments and methods to measure continuously electromagnetic radiation emitted from the human body which is spectrally modified by the presence of blood glucose utilizing narrow band and/or neutral density filters for detection of said radiation in the infrared spectral region.

It is yet still another object of this invention to correlate the state of continuous measured emission spectral characteristic with blood glucose concentrations.

The present inventions are built on the fact that the human body naturally emits strong electromagnetic radiation in the micrometer wavelengths and is based on the discovery that said radiation consists of spectral information of the blood analyte (e.g. glucose) or other tissue analyte and can be directly correlated with the blood analyte (e.g. glucose) or other tissue analyte concentrations. This spectrally significant emission which shows blood glucose concentration spectral dependence is measured by an infrared detector located in a remote sensor assembly mounted in a subject's ear canal.

The human body emits strong electromagnetic radiation based on the law of physics which states that all objects emit infrared radiation, and the infrared radiation amounts and spectral characteristics of the object are determined by their absolute temperatures as well as by the properties and states of the object.

Planck's law states a relationship between the radiant intensity, spectral distribution, and temperature of the blackbody as follows:

$$W_0(\lambda,T) = 2\pi c^2 h/\lambda^5 (e^{hc/k\lambda T}-1)^{-1}$$

where:
$W_0(\lambda,T)$—spectral radiant emittance [W/cm² $\mu$m],
T—absolute temperature of blackbody [K],
$\lambda$—wavelength of radiation [$\mu$m],
c—velocity of light=$2.998 \times 10^{10}$[cm/sec],
h—Plank's constant=$6.625 \times 10^{-34}$ [W sec²],
k—Boltzman's constant=$1.380 \times 10^{-23}$ [W sec/K].

As temperature rises, the radiation energy is increased as is shown on FIG. 1. The radiation energy varies depending on wavelengths. The peak value of the radiant emittance distribution shifts to the short wavelengths side with an increase in temperature, and radiation occurs over a wide wavelength band.

The ratio of spectral radiant emittance W(λ,T) at a particular wavelength of the non-blackbody radiation to spectral radiant emittance $W_0(\lambda,T)$ of the blackbody at the same wavelength and temperature is called monochromatic emissivity $\epsilon_\lambda$:

$$\epsilon_\lambda = \frac{W(\lambda,T)}{W_0(\lambda,T)}.$$

If the $\epsilon_\lambda$ is constant for all wavelengths, then this kind of body can be called a gray body. Usually in nature we have many materials whose properties are close to the properties of a gray body. For example, human skin tissue has an integral emissivity equal to about 0.986. For the tympanic membrane, which is very well supplied by blood and has very thin skin tissue penetrable by infrared radiation, the monochromatic emmissitivity will be modulated by the spectral characteristic of blood tissue and blood composition will influence it. Kirchhoff's law confirms that for the entire body in the same temperature and for the same wavelength absorptivity $A_\lambda$ is equal to monochromatic emissivity $\epsilon_\lambda$. Thus one can conclude that blood spectral absorption characteristics with different contents of glucose (or other analytes) shown on FIG. 2 will change the emissivity of the tympanic membrane. This makes it possible to measure the concentration of an analyte (e.g. glucose) in blood in the emission spectral lines characteristic to blood analyte emitted by the human body as heat.

Radiation from the human body possesses information about spectral characteristics of the object and is determined by absolute body temperatures as well as by the properties and states of the emitting body tissue.

One can measure radiation from the skin of the human body or, more reliably, quantify the infrared emission from the tympanic membrane. The tympanic membrane is known to be in an excellent position for the measurement of, for example, body temperature because it shares its blood supply with the hypothalamus, the center of core body temperature regulation. The tympanic thermometer measures the integral intensity of infrared radiation and uses the ear. It is inserted into the auditory canal so as to sufficiently enclose the detector apparatus such that multiple reflections of radiation from the tympanic membrane transform the auditory canal into a "black body" cavity, a cavity with emissivity theoretically equal to one. In this way a sensor can get a clear view of the tympanic membrane and its blood vessels for measuring the amount of infrared radiation emitted by the patient's tympanic membrane. This infrared radiation is spectrally modified by the tissue when compared with the theoretical blackbody radiation as shown above in Planck's and Kirchhoff's laws. Thus infrared radiation has the spectral characteristics of, for example, blood in the tympanic membrane. This allows measurements of the concentration of blood constituencies by spectral analysis of infrared radiation naturally emitted from the human body.

Spectral characteristics included in electromagnetic radiation from the human body involve information on all components of the tissue. In the invented instrument, spectral characteristics of various constituencies of the tissue will be separated using the concept of non-dispersive correlation spectroscopy methods. It relies on the use of adequate filters placed in front of an infrared detector. Electrical output signal from the infrared detector provides a measure proportional to analyte concentration and can show for example, the concentration of glucose in blood tissue.

BRIEF DESCRIPTION OF THE DRAWINGS

FIG. 4 is a diagram of an infrared radiation detection system of the embodiment of the invention:
  a) of a single element detector system;
  b) of a dual element detector system;
  c) top view of the single element detector system;
  d) top view of the dual element detector system.

DESCRIPTION OF THE PREFERRED EMBODIMENT

The present invention is directed at an instrument and method for the continuous non-invasive detection of the concentration of analytes in human body tissues, for example, glucose in blood, using naturally occurring infrared radiation in the micrometer spectral region of the human body.

The invented instrument will measure continuously infrared radiation emitted naturally by the human body. This infrared radiation contains spectral information of the emitting body tissue. The radiation thermometer measures the integral energy of infrared radiation from the body through the entire infrared wavelengths without spectral discrimination. In the case of the invented instrument the signal from the detector is proportional to the intensity of the spectrum emitted from the body passing through the filter with the spectral characteristic of the measured analyte, for example, glucose in blood. In the other embodiment of the invention, the intensity of the infrared spectrum emitted from the body is passing through a filter with spectral characteristics which do not include spectral bands of the analyte. It establishes reference point for more accurate measurements.

Figure 1:
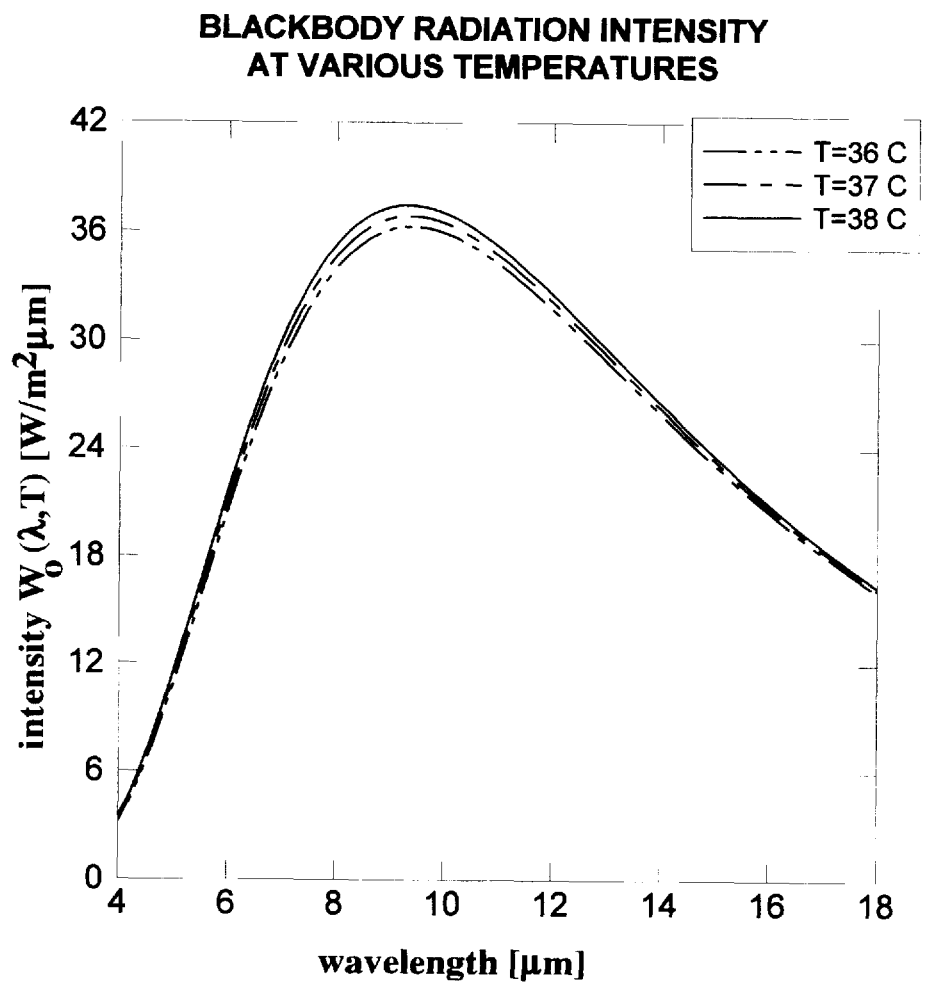
FIG. 1 is a graph showing spectral changes in intensity and in the infrared wavelength spectrum depending on the temperature of the blackbody object at the range of physiological human body temperatures.

In FIG. 1 is a graph showing spectral characteristics of blackbody radiation for different temperatures within the human body's physiological range in the infrared spectral region of interest.

Figures 2A, 2B, 2C, 2D:
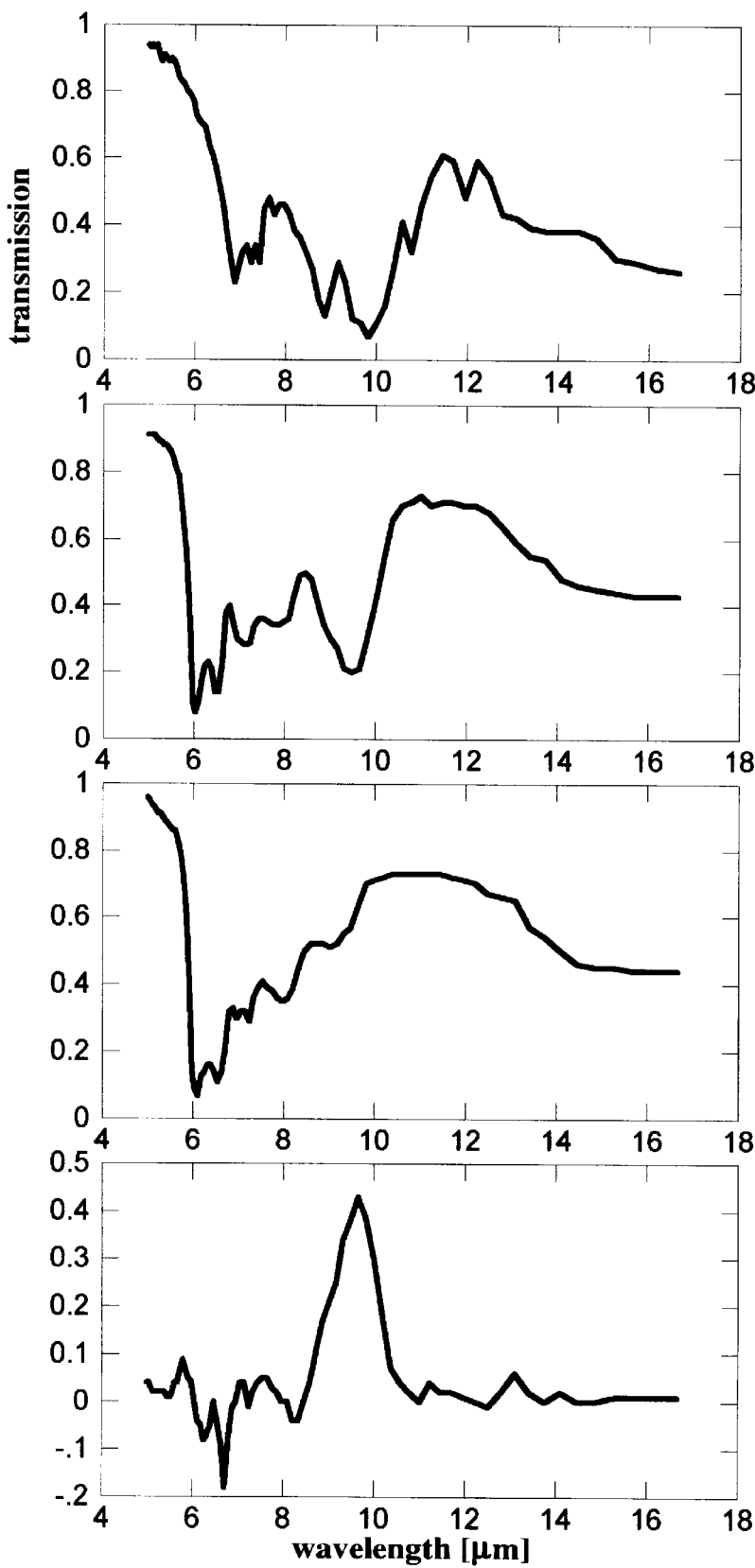
FIG. 2 is an infrared absorption spectrum:
  a) of D-glucose;
  b) of dried human blood with a high level of glucose content;
  c) of dried human blood with a low level of glucose content;
  d) of the differential spectrum between a high and low level of glucose content in dried human blood.

In FIG. 2a is shown the infrared absorption spectrum of D-glucose. Setting the filter for significant emission lines of analyte in one of the windows of the infrared detector system and using an appropriate attenuation filter to compensate for the difference in integral intensity absorbed by the first filter, the instrument will measure the concentration of glucose in the human body emitting natural electromagnetic radiation in the infrared spectral region.

In FIG. 2b is shown an infrared spectrum of dried blood with a high level of glucose content and, in FIG. 2c, one with a low level of blood glucose. A difference spectrum of curve b and curve c is shown in FIG. 2d. The curve in FIG. 2d is the difference spectrum between a high and low content of glucose in dried blood. These spectral absorption characteristics will influence the emissivity of human radiation.

Figure 3A:
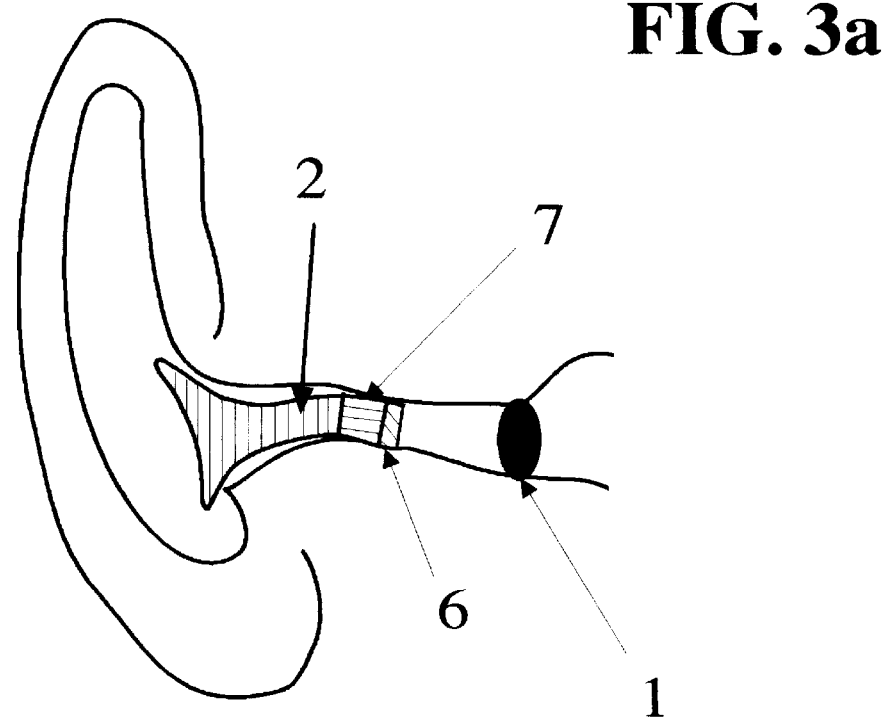
FIG. 3 is a simplified diagram of an embodiment of an instrument of the invention;
  a) remote sensor assembly inserted in ear canal
  b) analyzing electronics microcomputer system and display
Figure 3B:
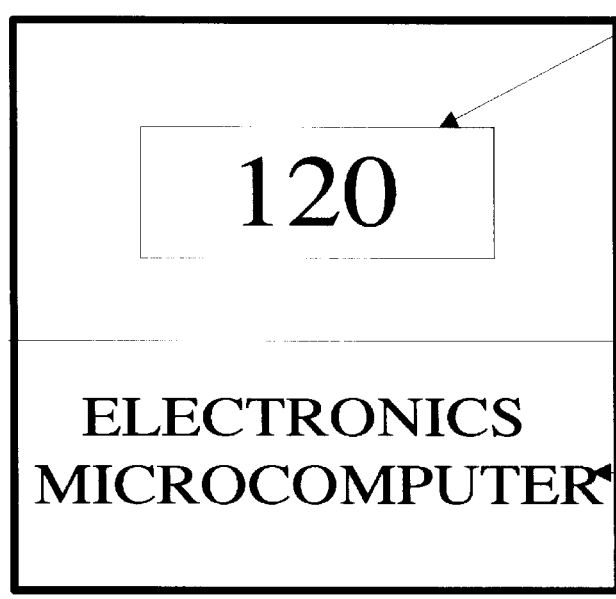

In FIG. 3a and FIG. 3b is shown a simplified diagram of an embodiment of the invented instrument. Infrared radiation from the object target 1 such as a human body tympanic membrane is optically received by a remote sensor assembly inserted in a subject's ear canal. The infrared radiation sensor is contained within an ear plug remote assembly 2 which is connected with an electronic analyzing unit 3 by cable or by a telemetric transmitting/receiving system. The instrument consists of the ear plug 2 for insertion into an ear canal with the infrared radiation sensor detecting system, and electronic analyzing unit 3 consisting of: electronics with a microcomputer 4 and a display system 5. The ear plug assembly 2 optionally would consist of the telemetric transmitting electronics while the electronic analyzing unit 3 optionally would consist of the telemetric receiving electronics. The infrared radiation sensor detecting system consists of an optical infrared filter set 6 and a infrared detector 7 sensitive in the infrared region of human body radiation. This infrared radiation sensor (detector 7) can be of any type known to the art which allows continues measurement of infrared energy including the thermopile sensor. This sensor generates an electrical output signal which is representative of the received infrared radiation. The electronics with microprocessor 4 and the display system 5 must stabilize the temperature dependent parts of the instrument, compensate for the ambient temperature changes, correlate, calculate and then display the concentration of the analyte from the spectral intensity measurements of the infrared radiation emitted by the body. The electronics with microprocessor 4 can be optionally connected directly to a regulated insulin reservoir such as an insulin pump or an artificial pancreas for an automatic insulin control system.

The infrared radiation detection system consists, for example, of the single element type PS20, PL82 or PC1 series thermopile detector from Meggitt Avionics Inc., Manchester, N.H., with one sensing area 8 covered by a silicon window 9 with a long pass filter (to pass only infrared radiation which corresponds to emission in the range of the internal temperature of a human body) as shown schematically on FIG. 4a and FIG. 4c. A radiation thermopile detector is a collection of thermocouples of two dissimilar metals connected in a series. The active, or "hot," junctions of the detectors are blackened to efficiently absorb radiation, while the reference, or "cold," junctions are maintained at the ambient temperature of the detector 7 base 16. The absorption of the radiation, by the blackened area, causes a rise in the temperature of the hot junctions, as compared to the cold junctions. The difference in temperature causes the detector to generate a voltage. The cold junction connected with the base 16 of the detector 7 may also be thermally coupled with a reference absolute temperature sensor, for example, thermistor. The front of the infrared radiation sensing area is covered by an appropriate infrared bandpass filter 10 with a spectral characteristic significant for emission lines of the measured analyte. The sensor base 16 or housing attached to cold junctions are in thermal contact with the body e.g. with the ear canal. Infrared radiation from the tympanic membrane 1 after passing through the bandpass filter 10 illuminates the hot junction causing a rise in the temperature of the hot junction. The cold junction in thermal contact with the base 16 and the body having a relatively large thermal mass establishes the reference points in comparison to which, spectrally modified by concentration of analyte changes, infrared radiation is measured.

In the other embodiment of the invention the detection system consists, for example, of the dual element type P62D, PL64D series thermopile detector from Meggitt Avionics Inc., Manchester, N.H., with two sensing areas 11 and 12 covered by a silicon window 13 with a long pass filter (to pass only infrared radiation which corresponds to emission in the range of the internal temperature of a human body) as shown schematically on FIG. 4b and FIG. 4d. One of the sensing elements 11 is covered by a negative correlation filter 14 when the other sensing area 12 is covered by an appropriate attenuation filter 15 which does not have spectral bands characteristic to the measured analyte. Spectrally modified infrared radiation from, for example, the tympanic membrane 1 illuminates both windows, one with a negative correlating filter 14 which blocks radiation in the emission bands for the analyte to be measured and the other which passes through a neutral density filter 15 capable of blocking radiation equally at all wavelengths in the range of interest. This is to compensate for the overall attenuation by the negative correlating filter in the first sensing area. The two sensing areas 11 and 12 of the detector 7, whose top view is shown on FIG. 4d, are connected so that their outputs are subtracted. The difference of the radiation intensity between the two radiation paths provides a measure proportional to the analyte concentration. The cold junction of both sets of thermopiles connected to the base 16 are kept in thermal contact with the body ear canal as shown schematically in FIG. 3a. This stabilizes the overall output signal from the detector 7 and makes it independent of the ambient temperature.

The electrical signal from the detector is then sent by cable or by a remote transmitting/receiving system to the analyzing electronics microcomputer system 4 and to the display 5 as shown in FIG. 3b. The intensity of this signal is proportional to the spectral difference measured by the detector and thus proportional to the concentration of the body analyte.

In the other embodiment of the invention the detection system consists of a narrow band filter with the spectral emission characteristic of glucose in blood in sensing area (11 or 12) in front of one of the windows and an appropriate attenuation filter or another narrow band filter with a spectral characteristic at a wavelength not sensitive for analyte concentration in front of the other window. The two sensing areas 11 and 12 of the detector 7, whose top view is shown on FIG. 4d, are connected so that their outputs are subtracted. The difference of the radiation intensity between the two radiation paths with different narrow band filters provides a measure proportional to the analyte concentration. The cold junction of both sets of thermopiles connected to the base 16 are in thermal contact with the body ear canal. This stabilizes the overall output signal from the detector 7 and makes it independent of the ambient temperature.

The display unit of the instrument will have a crucial role during day-to-day operations and will display the concentration of blood glucose for measurements in diabetic patients. A computer may also store information for keeping records of the measurement of the patient's blood glucose levels.

The embodiments of the present invention are intended to be merely exemplary and those skilled in the art should be able to make variations and modifications without departing from the spirit of the present invention. All such variations and modifications are intended to be within the scope of the present invention as defined in the appended claims.

What is claimed is:

1. A method of determining continuously a human body tissue analyte concentration by non-invasive measurement of emission spectral lines characteristic to a body tissue analyte in an infrared spectral region emitted naturally by a human body as heat, comprising:

a. measuring continuously a spectral intensity of said emission lines;

b. said emission spectral lines having a wavelength dependence of tissue constituents;

c. detecting continously the emission spectral lines at a predetermined emission wavelength;

d. analyzing the emission spectral lines in said infrared spectral region;

e. correlating said spectral intensity of emission spectral lines with body analyte concentration.

2. The method as in claim 1, for determining blood glucose concentration continuously by non-invasive measurements of emission spectral lines characteristic to a body tissue analyte in an infrared spectral region emitted naturally by a human body's tympanic membrane in an infrared wavelength spectrum as heat.

3. An instrument for determining continuously a human body tissue analyte concentration by non-invasive measurement of emission spectral lines characteristic to a body tissue analyte in an infrared spectral region emitted naturally by a human body as heat, comprising:

a. a means for detecting continuously said emission spectral lines at a predetermined infrared wavelength;

b. a means for detecting continuously a spectral intensity of the emission spectral lines;

c. a means for correlating the intensity of emission spectral lines with the tissue analyte concentration.

4. The instrument of claim 3 wherein the detecting means comprises a detector means and an analyzing means for wavelength selecting means of the emission spectral lines; detector means for detecting continuously the intensity of received emission spectral lines from said analyzing means producing an electrical output signal; and wavelength selecting means for allowing only significant wavelengths of tissue analyte emission spectral lines in natural infrared radiation emitted by the human body to reach the detector means.

5. The instrument of claim 4, wherein the detector means is infrared energy sensors for continuous infrared energy measurements.

6. The instrument of claim 4, wherein the analyzing means comprises filter means for filtering the emission spectral lines to allow only for wavelengths significant to the tissue analyte emission spectral lines to pass or to be absorbed before reaching the detector means.

7. The instrument of claim 2, where the correlating means is —an electronic device comprising—electronics and a microcomputer for correlating—a—state of—an— electronic output signal from the detecting means with the tissue analyte concentration.

8. The instrument as in claim 3, for determining blood glucose concentration continuously by non-invasive measurements of emission spectral lines characteristic to a body tissue analyte in an infrared spectral region emitted naturally by a human body's tympanic membrane in an infrared wavelength spectrum as heat.

9. An instrument for non-invasive continuous tissue analyte concentration measurements based on measurements of emission spectral lines characteristic to a human body tissue analyte in an infrared spectral region emitted naturally by a tympanic membrane as heat, comprising:

a. an ear plug assembly for insertion into an ear canal;

b. said ear plug assembly consisting of an infrared radiation detecting system consisting of an optical infrared filter set and a detector sensitive in an infrared region of human body heat radiation for continuously detecting the emission spectral lines;

c. a base of the detector adapted to be in conductive contact with a human body;

d. said ear plug assembly connected with electronics, a microcomputer and a display system for forming, calculating, and displaying an electrical signal from the detector to show a numerical value of the analyte concentration.

* * * * *